US011191525B2

(12) United States Patent
Veronesi et al.

(10) Patent No.: US 11,191,525 B2
(45) Date of Patent: Dec. 7, 2021

(54) METHOD AND SYSTEM FOR VISUALIZING OVERLAPPING IMAGES

(71) Applicant: General Electric Company, Schenectady, NY (US)

(72) Inventors: Federico Veronesi, Bologna (NO); Olivier Gerard, Oslo (NO)

(73) Assignee: General Electric Company, Schenectady, NY (US)

( * ) Notice: Subject to any disclaimer, the term of this patent is extended or adjusted under 35 U.S.C. 154(b) by 214 days.

(21) Appl. No.: 16/100,967

(22) Filed: Aug. 10, 2018

(65) Prior Publication Data
US 2020/0046324 A1 Feb. 13, 2020

(51) Int. Cl.
*A61B 8/08* (2006.01)
*G06T 7/40* (2017.01)
*G06T 5/50* (2006.01)

(52) U.S. Cl.
CPC .............. *A61B 8/5253* (2013.01); *G06T 5/50* (2013.01); *G06T 7/40* (2013.01); *G06T 2207/10132* (2013.01)

(58) Field of Classification Search
CPC ....... A61B 8/463; A61B 8/5253; G06T 19/00; G06T 2207/10072; G06T 2207/10132; G06T 2210/41
See application file for complete search history.

(56) References Cited

U.S. PATENT DOCUMENTS

| | | | |
|---|---|---|---|
| 6,466,224 B1 | 10/2002 | Nagata | |
| 6,690,371 B1* | 2/2004 | Okerlund | G06T 11/008 345/424 |
| 8,090,168 B2 | 1/2012 | Washburn et al. | |
| 2005/0059894 A1 | 3/2005 | Zeng | |
| 2007/0230761 A1 | 10/2007 | Gundel | |
| 2008/0278489 A1* | 11/2008 | Mielekamp | A61B 6/504 345/424 |
| 2010/0128988 A1* | 5/2010 | Kincaid | G06K 9/6253 382/199 |

(Continued)

FOREIGN PATENT DOCUMENTS

JP 2017146758 A 8/2017
WO 20120117286 W 9/2012

OTHER PUBLICATIONS

JP2017-146758 English translation of Abstract; obtained from Espacenet Jan. 26, 2021; 1 page.

(Continued)

*Primary Examiner* — Ross Varndell

(57) ABSTRACT

A medical imaging workstation and a method for visualizing overlapping images includes accessing a first image data set and a second image data set. The workstation and method includes displaying a first image on a display device, where the first image includes at least a portion of the first image data set and includes a structure. The workstation and method includes displaying a second image on the display device at the same time as the first image, where the second image includes at least a portion of the second image data and includes the structure, and where at least a portion of the second image overlaps the first image. The workstation and method includes automatically cyclically varying an opacity of the at least the portion of the second image that overlaps the first image.

17 Claims, 8 Drawing Sheets

(56) References Cited

U.S. PATENT DOCUMENTS

| | | | |
|---|---|---|---|
| 2012/0218290 A1* | 8/2012 | Waschbuesch | G06T 5/009 345/619 |
| 2014/0187948 A1* | 7/2014 | Gerard | A61B 8/5207 600/443 |
| 2016/0206291 A1* | 7/2016 | Yang | |
| 2018/0225862 A1* | 8/2018 | Petkov | G06T 15/06 |

OTHER PUBLICATIONS

PCT application PCT/US2019/044598 filed Aug. 1, 2019—International Search Report/Written Opinion dated Nov. 28, 2019, 12 pages.

* cited by examiner

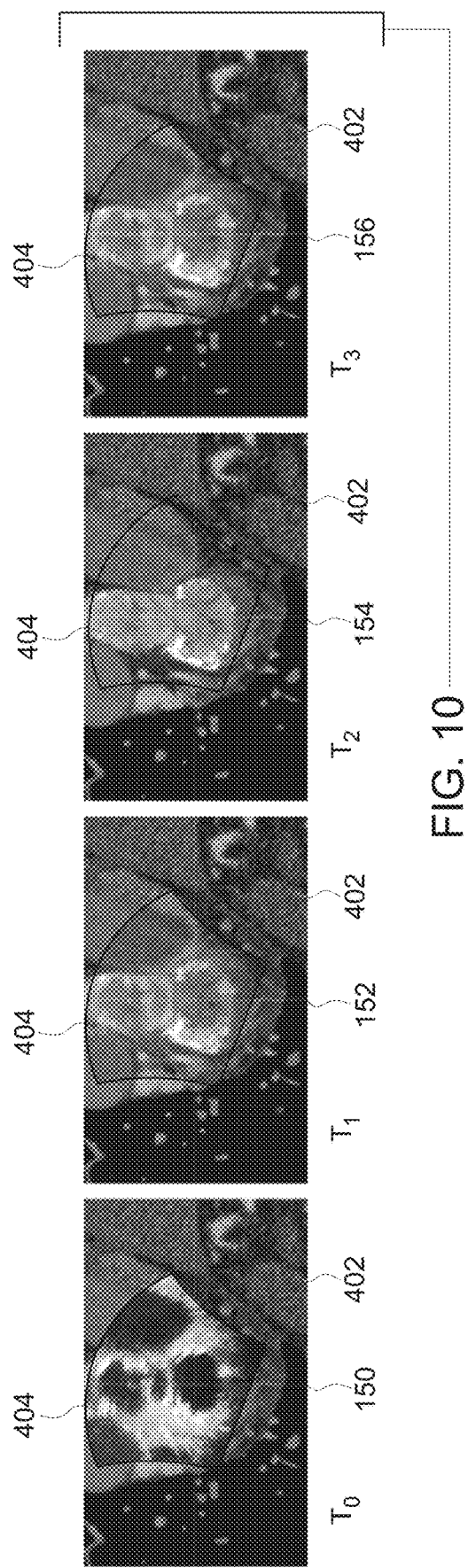

METHOD AND SYSTEM FOR VISUALIZING OVERLAPPING IMAGES

FIELD OF THE INVENTION

This disclosure relates generally to a method and medical imaging workstation for visualizing overlapping images.

BACKGROUND OF THE INVENTION

The invention relates generally to imaging of an object, and more specifically to visualizing overlapping images.

In medical imaging, it is oftentimes desirable to display two or more overlapping images. For example, two images may be displayed in an overlapping fashion when attempting to register a first image to a second image. Likewise, a first image containing a first type of data may be displayed as overlapping with a second image containing a second type of data. The two overlapping images may contain information acquired with different imaging modalities or the two overlapping images may contain information acquired in different acquisition modes.

One problem with conventionally displayed overlapping images is that the overlying image at least partially obscures the underlying image. The overlying image makes it more difficult to see the information contained in the underlying image. Or, conversely, if the overlying image is made to be more transparent, the data contained in the overlying image is more difficult to interpret. It is difficult or impossible to display all the information in both the overlying and the underlying images using conventional techniques.

It is typical to display images in an overlapping manner when registering a first image to a second image. When registering two images to each other, it is desired to align common anatomical structures or landmarks between the two images. The process of registering two images often requires manual inputs from an operator in order to register the images to each other as closely as possible. However, it is difficult to accurately register two images to each other when the overlying image obscures portions the underlying image. It is very difficult for a user to discern anatomical structures in both the overlying image and the underlying image in order to accurately register them to each other.

Likewise, when the underlying and the overlying images represent different types of data, it is difficult for the user to interpret all of the data in both the underlying image and the overlying image.

For at least the reasons discussed hereinabove, there is a need for an improved method and workstation for visualizing overlapping images.

BRIEF DESCRIPTION OF THE INVENTION

The above-mentioned shortcomings, disadvantages and problems are addressed herein which will be understood by reading and understanding the following specification.

In an embodiment, a method for visualizing overlapping images includes accessing a first image data set and a second image data set, wherein the first image data set and the second image data set were acquired with one or more medical imaging systems. The method includes displaying a first image on a display device, wherein the first image includes at least a portion of the first image data set and a structure. The method includes displaying a second image on the display device at the same time as the first image, wherein the second image comprises at least a portion of the second image data set and includes the structure, and wherein at least a portion of the second image overlaps the first image. The method includes automatically cyclically varying an opacity of at least the portion of the second image that overlaps the first image.

In an embodiment, a medical imaging workstation includes a user input device, a display device, and a processor in electronic communication with both the user input device and the display device. The processor is configured to access a first image data set and a second image data set, where the first image data set and the second image data set were acquired with one or more medical imaging systems. The processor is configured to display a first image on the display device, wherein the first image includes at least a portion of the first image data set and includes a structure. The processor is configured to display a second image on the display device at the same time as the first image, where the second image includes at least a portion of the second image data set and includes the structure, and wherein at least a portion of the second image overlaps the first image. The processor is configured to automatically cyclically vary an opacity of at least the portion of the second image that overlaps the first.

Various other features, objects, and advantages of the invention will be made apparent to those skilled in the art from the accompanying drawings and detailed description thereof.

BRIEF DESCRIPTION OF THE DRAWINGS

FIG. 10 is a representation of a series of screen shots in accordance with an embodiment;

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
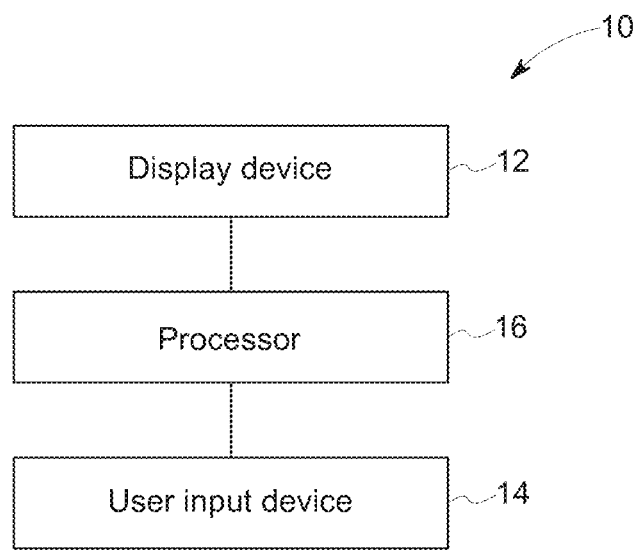
FIG. 1 is schematic representation of a workstation in accordance with an embodiment.

FIG. 1 is a schematic diagram of a medical imaging workstation 10 in accordance with an embodiment. The medical imaging workstation 10 includes a display device 12, a user input device 14, and a processor 16. Both the display device 12 and the input device 14 are in electronic communication with the processor 16. The display device 12 may be a LED display, an OLED display, a liquid crystal display (LCD) a projection display device, a cathode ray tube monitor, or any other type display configured for displaying one or more images. The user input device 14 may include any type of user input control including one or more of: a mouse, a trackball, a keyboard, a touch pad, a touchscreen-based user interface, one or more hard buttons, sliders, rotaries, or any other type of physical control. The processor 16 may include a one or more of the following elements: a microprocessor, a central processing unit (CPU), a graphics processing unit (GPU), a graphics card, or any other type of electronic device configured to implement logical processing instructions. According to various embodiments, the medical imaging workstation 10 may be a stand-alone workstation that is configured to received image data from one or more of a memory, a separate medical imaging system, and/or a database such as a PACS/RIS system.

Figure 2:
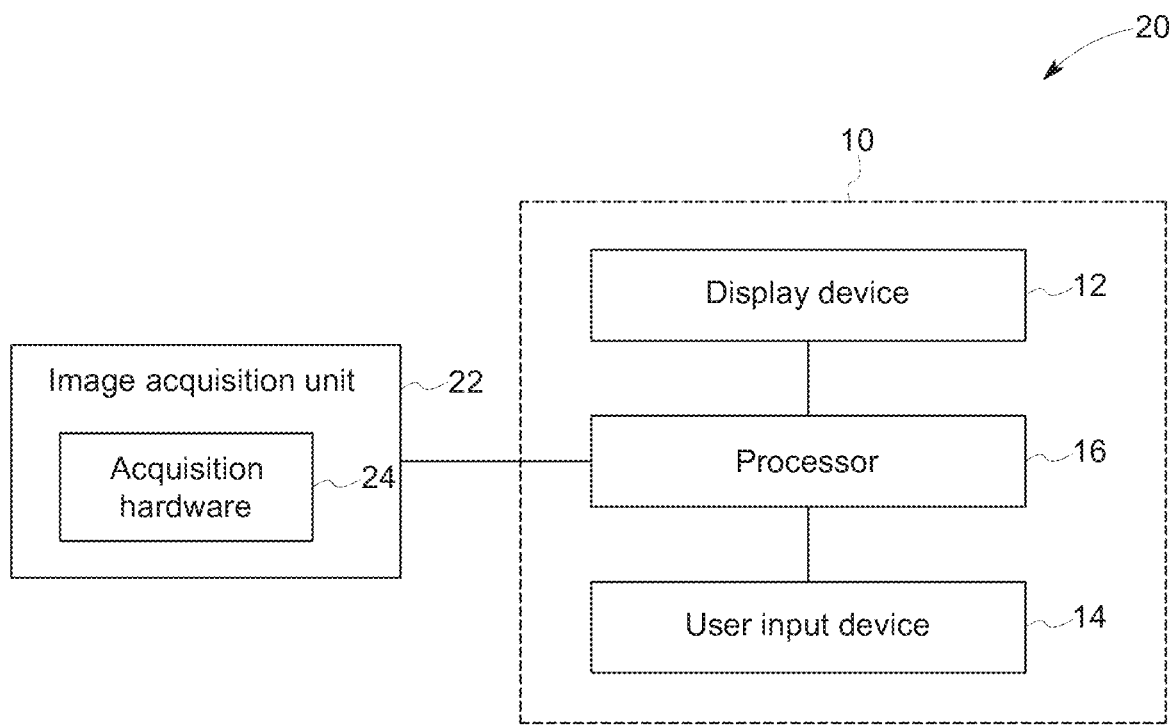
FIG. 2 is a schematic representation of a medical imaging system in accordance with an embodiment.

FIG. 2 is a schematic diagram of a medical imaging system 20. The medical imaging workstation 10 is a component of a medical imaging system 20 according to an embodiment. The medical imaging system 20 also includes an image acquisition unit 22. The medical imaging system 20 may be any type of medical imaging system such as an x-ray imaging system, a computed tomography (CT) imaging system, a positron emission tomography (PET) imaging system, an ultrasound imaging system, or a single photon computed tomography (SPECT) imaging system. Likewise, the image acquisition unit 22 may be an x-ray acquisition unit, a computed tomography (CT) acquisition unit, a positron emission tomography (PET) acquisition unit, an ultrasound acquisition unit, a single photon computed tomography (SPECT) acquisition unit, or any other type of medical image acquisition unit. The image acquisition unit 22 includes acquisition hardware for acquiring one or more image data sets and hardware structures for supporting the acquisition hardware. The image acquisition unit may also include one or more processors for controlling the acquisition of image data. According to various embodiments, the processor 16 in the medical imaging workstation may also be used to control the acquisition hardware 24 in the image acquisition unit 22.

According to an embodiment where the image acquisition unit 22 is an x-ray acquisition unit, the acquisition hardware 24 may include an x-ray tube and an x-ray detector.

According to an embodiment where the image acquisition unit 22 is a CT acquisition unit, the acquisition hardware 24 may include one or more x-ray tubes and a CT detector disposed on a gantry configured to rotate about a patient support. The CT detector is configured to detect x-ray emitted by the one or more x-ray tubes.

According to an embodiment where the image acquisition unit 22 is PET acquisition unit, the acquisition hardware 24 may include a PET detector disposed about a patient gantry. The PET detector is sensitive to gamma rays emitted in response to a positron annihilation event occurring within a patient.

According to an embodiment where the image acquisition unit 22 is a SPECT acquisition unit, the acquisition hardware 24 may include one or more gamma detectors configured to detect gamma rays emitted from a radioactive tracer.

According to an embodiment where the image acquisition unit 22 is an ultrasound acquisition unit, the acquisition hardware 24 may include a probe with a plurality of transducer elements, a beamformer, a transmitter, and a receiver.

Figure 3:
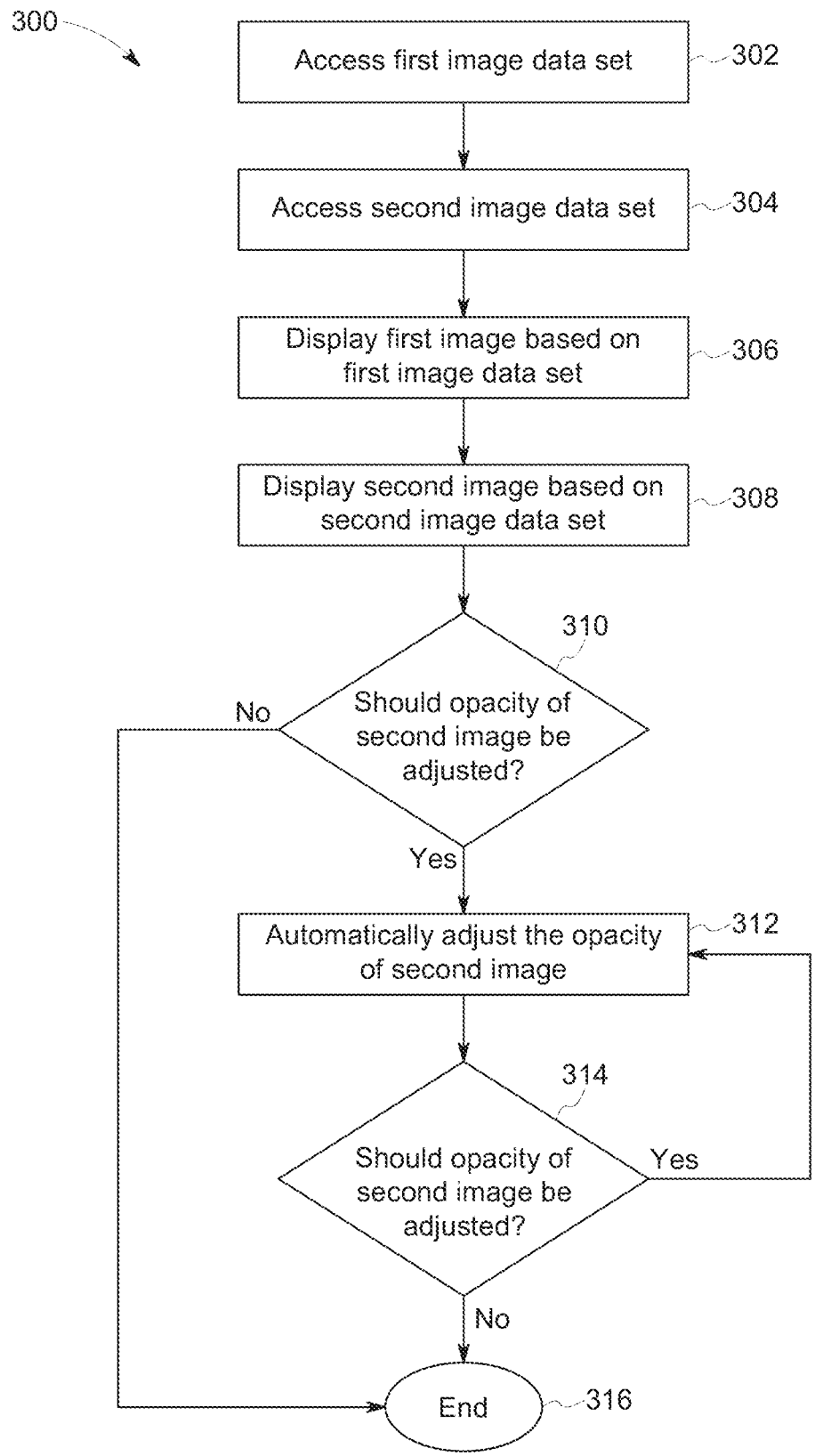
FIG. 3 is a flow chart of a method in accordance with an embodiment.

FIG. 3 is a flow chart of a method 300 in accordance with an exemplary embodiment. The individual blocks of the flow chart represent steps that may be performed in accordance with the method 300. Additional embodiments may perform the steps shown in a different sequence and/or additional embodiments may include additional steps not shown in FIG. 3. The technical effect of the method 300 is cyclically varying the opacity of at least a portion of an image that is overlapped with another image in order to more clearly show the information in both an overlying image and an underlying image. The method 300 will be described according to exemplary embodiments using the workstation 10 shown in FIGS. 1 and 2.

At step 302, the processor 16 accesses a first image data set. The first image data set may be acquired with a separate medical imaging system and the processor 16 may access the first image data set from a memory, the first image data set may be accessed from a separate medical imaging system, or the first image data set may be accessed from a PACS/RIS system. Or, according to embodiments where the workstation 10 is part of a medical imaging system, such as the embodiment shown in FIG. 2, the first image data may be acquired with the image acquisition unit 22. The processor 16 may control the acquisition of the first image data set according to various embodiments.

At step 304, the processor 16 accesses a second image data set. The second image data set may be acquired with a separate medical imaging system and the processor 16 may access the first image data set from a memory, a separate medical imaging system, or from a PACS/RIS system. Or, according to embodiments where the workstation 10 is part of a medical imaging system, such as the embodiment shown in FIG. 2, the second image data set may be acquired with the image acquisition unit 22. The processor 16 may control the acquisition of the first image data set according to various embodiments. The first image data set and the second image data set may include at least one structure in common. For example, one or more anatomical structures included in the first image data set may also be included in the second image data set.

The first image data set and the second image data set may be acquired with different medical imaging systems, according to an embodiment. For example, the first image data set may be acquired with a medical imaging system selected from a list including an x-ray imaging system, a CT imaging system, a PET imaging system, an ultrasound imaging system, or a SPECT imaging system. The second image data set may, for instance, be acquired with a different type of medical imaging system. For example, the second image data set may be acquired with an x-ray imaging system, a CT imaging system, a PET imaging system, an ultrasound imaging system, or a SPECT imaging system, where the type of medical imaging system used to acquire the second image data set is different than the type of medical imaging system used to acquire the first image data set.

According to some nonlimiting examples, x-ray images acquired by x-ray imaging systems, CT images acquired by CT imaging systems, and MR images acquired by MR imaging systems provide images of structures represented in the body. PET images acquired by PET imaging systems and SPECT images acquired by SPECT imaging system are functional images which provide physiological information about a patient's body. Ultrasound images acquired by ultrasound imaging systems may be used to provide information about either structural features or physiological information, such as blood flow, strain, or tissue stiffness while imaging a patient, as well as other types of information. X-ray imaging systems and ultrasound imaging systems may both be used to provide real-time images of the patient during a procedure or an examination. The various different type of imaging systems are oftentimes referred to as modalities.

According to other embodiments, the first image data set and the second image data set may both be acquired with the same imaging modality. The first image data set may be acquired using the same or a different imaging mode. For example, the first image data set may be an ultrasound imaging data set acquired in a first imaging mode and the second image data set may be an ultrasound imaging data set acquired in a second imaging mode. Examples of ultrasound imaging modes include: B-mode, M-mode, color Doppler, strain, and elastography. According to an exemplary embodiment, the first image data set may be B-mode ultrasound imaging data and the second image data set may be color Doppler ultrasound imaging data.

At step 306, the processor 16 displays a first image based on at least a portion of the first image data set on the display device 12. And, at step 308, the processor 16 displays a second image based on at least a portion of the second image data set on the display device 12. The second image is at least partially overlapping with the first image on the display device. Steps 306 and 308 may be performed simultaneously.

Figure 4:
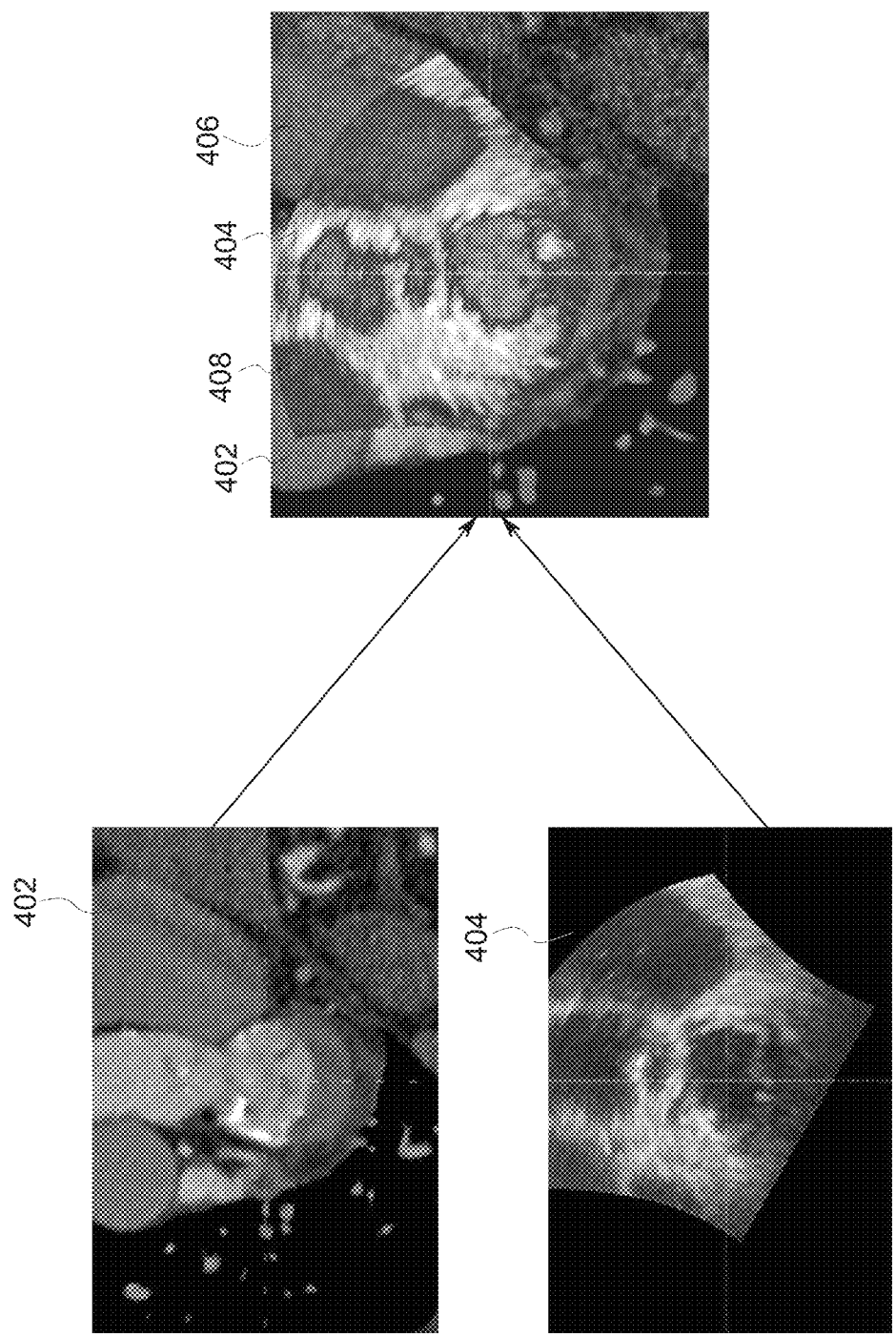
FIG. 4 is a representation of a first image, a second image, and a composite image.

FIG. 4 is a schematic representation of how the processor 16 may display both a first image and second image on the display device 12 at the same time. FIG. 4 shows a first image 402 generated based on the first image data set and a second image 404 generated based on the second image data set. FIG. 4 also shows composite image 406 which results from displaying both the first image 402 and the second image 404 at the same time on the display device 12. The second image 404 completely overlaps the first image 402 in the composite image 406 according to the embodiment shown in FIG. 4. According to other embodiments, the second image 404 may only partially overlap with first image 402 in the composite image 406. For these embodiments, there will be a portion of the second image 404 that overlaps the first image. According to some embodiments where the position of the second image 404 maybe adjusted with respect to the first image 402, the size and shape of the portion of the second image 404 that overlaps the first image 402 may change as the position of the second image 404 is adjusted with respect to the first image 402.

Region 408 represents the portion of the second image 404 that overlaps the first image 402 in the embodiment shown in FIG. 4. As discussed above, region 408 represents all of the second image 404 according to an exemplary embodiment. For purposes of this embodiment, the second image 404 will be referred to as the overlying image and the first image 402 will be referred to as the underlying image.

Figure 5:
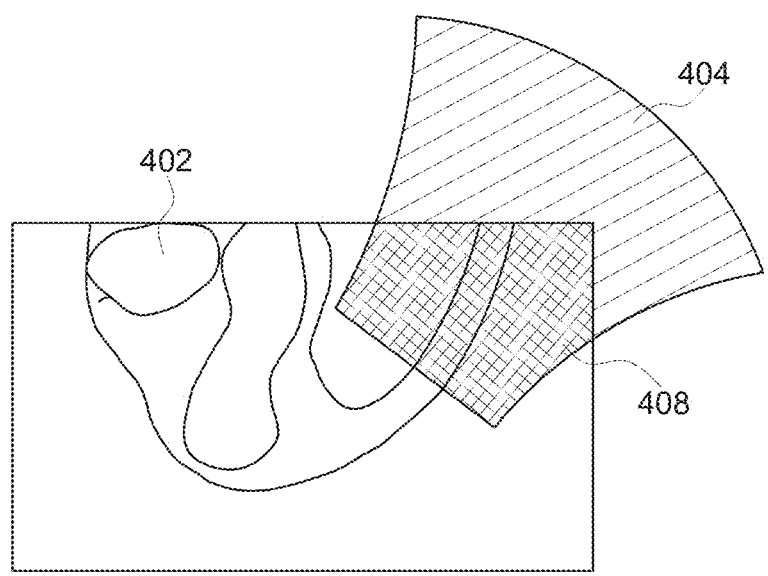
FIG. 5 is a representation of a second image overlapping a portion of a first image in accordance with an embodiment.

FIG. 5 shows a representation of an embodiment where only a portion of the second image 404 overlaps with the first image 402 according to an embodiment. In FIG. 5, the portion 408 of the second image 404 overlapping the first image 402 is shown with cross-hatching.

Figure 6:
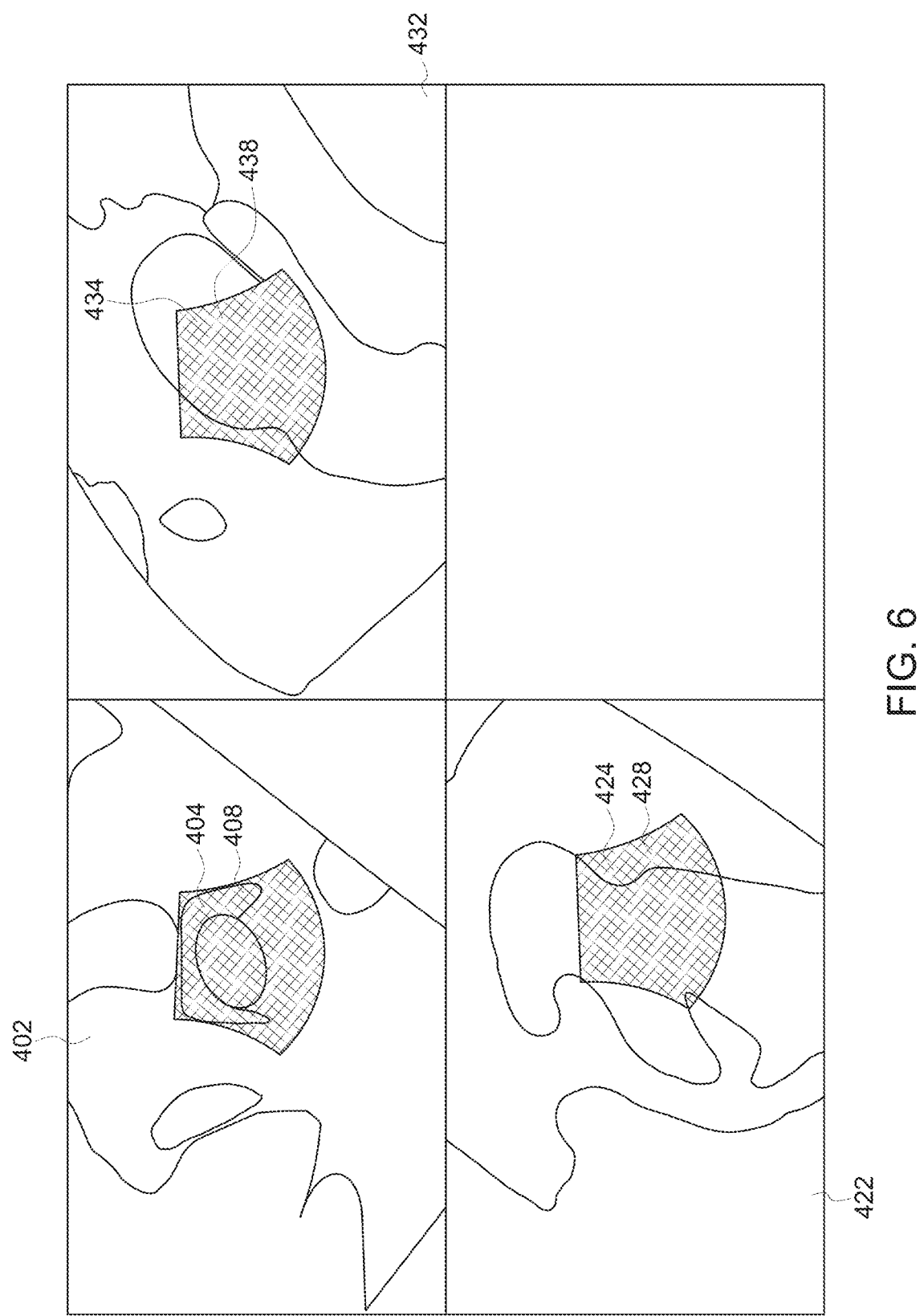
FIG. 6 is a representation of three composite images generated from 3D datasets in accordance with an embodiment.

FIG. 6 shows a representation of screenshot according to an embodiment where the first image data set is a 3D dataset and the second image data set is also a 3D dataset. Various embodiments may display multiple images representing various slices or planes at the same time. FIG. 6 includes overlapping images from three separate planes, or slices, within the first and second image datasets. The images in FIG. 6 represent different non-parallel planes, but according to other embodiments, the images may represent two or more planes that are parallel to each other from within the 3D datasets. For example, FIG. 6 includes the first image 402 and the second image 404 and a first overlapping region 408. According to an embodiment, the first image 402 may be a CT image of a mitral valve short-axis view and the second image 404 may be an ultrasound image of the mitral valve short-axis view. FIG. 6 includes a third image 422 and a fourth image 424 and a second overlapping region 428. According to an embodiment, the third image 422 may be a CT image of a mitral-commissural view and the first image 424 may be an ultrasound image of the mitral-commissural view. FIG. 6 includes a fifth image 432 and a sixth image 434 and a third overlapping region 438. According to an embodiment, the fifth image 432 may be a CT image of an antero-posterior long-axis view and the sixth image 434 may be an ultrasound image of the antero-posterior long axis view. The first image 402, the third image 422 and the fifth image 432 may all be generated by reconstructing planar views, or slices, from a 3D CT dataset. The second image 404, the fourth image 424 and the sixth image 434 may all be generated by reconstructing planar views from a 3D ultrasound dataset. It should be appreciated that according to other embodiments, images may be generated by reconstructing planar views, or slices, from different types of 3D datasets. Additionally, the views shown in FIG. 6 are according to an exemplary embodiment.

At 310, the processor 16 determines if the opacity of the second image 404 should be adjusted. According to an embodiment, if the workstation is in a mode that allows for automatically varying the opacity, then the method 300 advances to step 312. According to other embodiments, the user may be able to selectively toggle between a mode where the opacity of the second image 404 is automatically varied and a mode where the opacity of the second image 404 is not automatically varied. If it is not desired to adjust the opacity of the second image 404 (i.e., the workstation 10 is in a mode that does not automatically vary the opacity of the second image 404), then the method 300 advances to the end at 316.

If the workstation 10 is in a mode where the opacity of the second image is automatically varied, then the method 300 advances to step 312. At step 312, the processor 16 automatically adjusts the opacity of the second image 404 and the second image 404 is displayed on the display device 12 at an opacity that is different from the opacity of the second image 404 at step 308. The second image 404 may have either a uniform or a nonuniform opacity. For embodiments where the second image has a nonuniform opacity, the opacity of the image may still be decreased by either a fixed amount or by a percentage. At step 314, the processor 16 determines if it is desired to adjust the opacity of the second image. If it is not desired to adjust the opacity of the second image 404, the method advances to the end at step 316. If, however, the workstation 10 is still in a mode where the opacity of the second image 404 is automatically varied, then the method returns to step 312, where the opacity of the second image 404 is adjusted. The method 300 may iteratively cycle through steps 312 and 314 as long as the workstation 10 remains in a mode where automatically varying the opacity of the second image 404 is desired. According to some embodiments, the method may iteratively cycle through steps 312 and 314 while an operator is adjusting the position of the second image 404 with respect to the first image 402. Additional description about some exemplary ways that the opacity of the second image 404 may be automatically varied will be described hereinafter.

Figure 7:
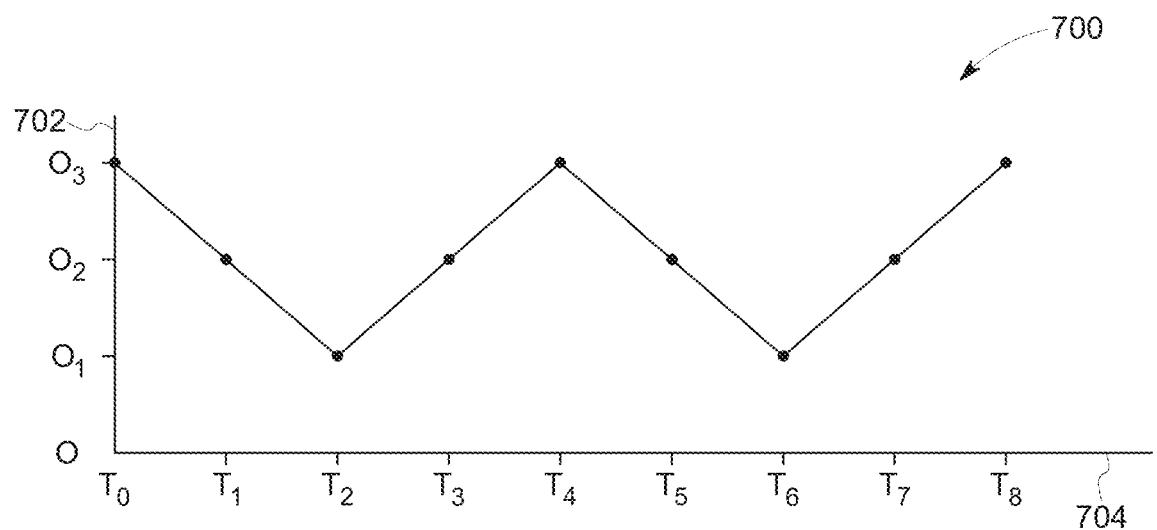
FIG. 7 is a graph of a sawtooth function in accordance with an embodiment.
Figure 8:
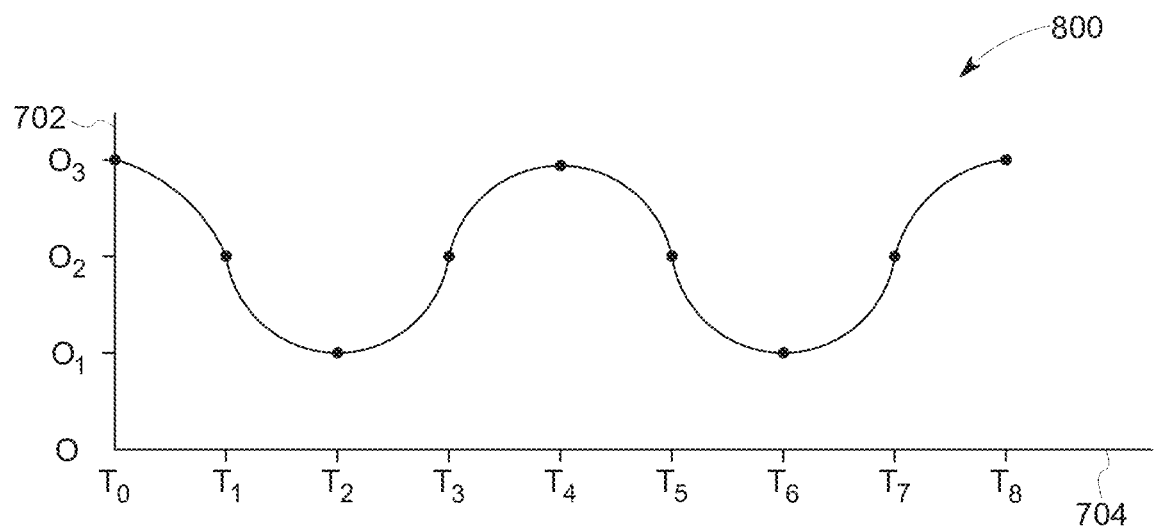
FIG. 8 is a graph of a sinusoidal function in accordance with an embodiment.
Figure 9:
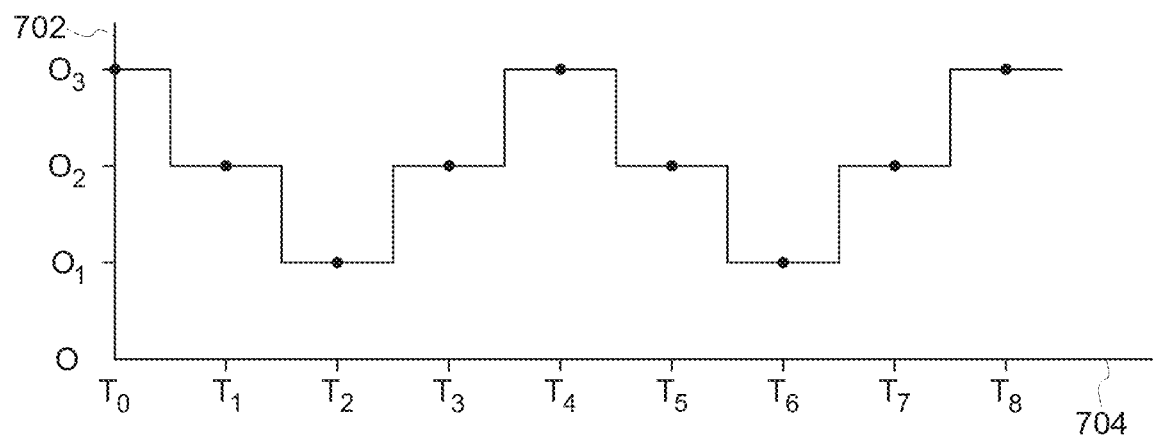
FIG. 9 is a graph of a step function in accordance with an embodiment.

FIG. 7, FIG. 8, and FIG. 9 are graphs showing ways that the processor 16 may cyclically vary the opacity of the second image according to various embodiments.

Referring to FIG. 7, the graph 700 represents opacity values along a y-axis 702 and time along an x-axis 704. $T_0$, $T_1$, $T_2$, $T_3$, $T_4$, $T_5$, $T_6$, $T_7$ and $T_8$ represent times along the x-axis 704. According to an embodiment, times $T_0$, $T_1$, $T_2$, $T_3$, $T_4$, $T_5$, $T_6$, $T_7$ and $T_8$ may represent evenly spaced intervals of time. The graph 700 represents a periodically repeating sawtooth function. From time $T_0$ to time $T_4$ represents one period $\tau$, or cycle. According to various embodiments, it may be desirable to use a function with a period that is between 1 and 20 seconds, although other embodiments may use functions with a period that is either shorter than 1 second or longer than 20 seconds. According to other embodiments, the period may be user adjustable. The graph 700 shows two complete cycles of the function represented in the graph 700.

According to the embodiment shown in FIG. 7, the processor 16 automatically cyclically varies the opacity of the second image 404 according to the sawtooth function represented by the graph 700. For example, at time $T_0$, the opacity of the second image 404 is $O_3$; at time $T_1$, the opacity of the second image is $O_2$; at time $T_2$, the opacity of the second image 404 is $O_1$; at time $T_3$, the opacity of the second image 404 is $O_2$; and at time $T_4$, the opacity of the second image 404 is $O_3$. From the time $T_0$ to the time $T_2$, the processor 16 decreases the opacity of the second image 404 in a linear manner and from the time $T_2$ to the time $T_4$, the processor 16 increases the opacity in a linear manner as shown in the graph 700.

Referring to FIG. 8, the graph 800 represents opacity values along the y-axis 702 and time along the x-axis 704. $T_0$, $T_1$, $T_2$, $T_3$, $T_4$, $T_5$, $T_6$, $T_7$ and $T_8$ represent times along the x-axis 704. According to an embodiment, times $T_0$, $T_1$, $T_2$, $T_3$, $T_4$, $T_5$, $T_6$, $T_7$ and $T_8$ may represent evenly spaced intervals of time. The graph 800 represents a sinusoidal function. From time $T_0$ to time $T_4$ represents one period, or cycle. According to various embodiments, it may be desirable to use a function with a period that is between 1 and 20 seconds, although other embodiments may use functions with a period that is either shorter than 1 second or longer than 20 seconds. According to other embodiments, the period may be user adjustable. The graph 800 shows two complete cycles of the sinusoidal function represented in the graph 700.

According to the embodiment shown in FIG. 8, the processor 16 automatically cyclically varies the opacity of the second image 404 according to the sinusoidal function as represented by the graph 800. For example, at time $T_0$, the opacity of the second image 404 is $O_3$; at time $T_1$, the opacity of the second image 404 is $O_2$; at time $T_2$, the opacity of the second image 404 is $O_1$; at time $T_3$, the opacity of the second image 404 is $O_2$; and at time $T_4$, the opacity of the second image 404 is $O_3$. From the time $T_0$ to the time $T_2$, the processor 16 decreases the opacity of the second image and from the time $T_2$ to the time $T_4$, the processor 16 increases the opacity in the manner shown in the graph 800.

Referring to FIG. 9, the graph 900 represents opacity values along the y-axis 702 and time along the x-axis 704. $T_0$, $T_1$, $T_2$, $T_3$, $T_4$, $T_5$, $T_6$, $T_7$ and $T_8$ represent times along the x-axis 704. According to an embodiment, times $T_0$, $T_1$, $T_2$, $T_3$, $T_4$, $T_5$, $T_6$, $T_7$ and $T_8$ may represent evenly spaced intervals of time. The graph 900 represents a step function. From time $T_0$ to time $T_4$ represents one period, or cycle. According to various embodiments, it may be desirable to use a function with a period that is between 1 and 20 seconds, although other embodiments may use functions with a period that is either shorter than 1 second or longer than 20 seconds. According to other embodiments, the period may be user adjustable. The graph 800 shows two complete cycles of the step function represented in the graph 700.

According to the embodiment shown in FIG. 8, the processor 16 automatically cyclically varies the opacity of the second image 404 according to the step function represented by the graph 800. For example, at time $T_0$, the opacity of the second image is $O_3$, at time $T_1$, the opacity of the second image 404 is $O_2$; at time $T_2$, the opacity of the second image 404 is $O_1$; at time $T_3$, the opacity of the second image 404 is $O_2$; and at time $T_4$, the opacity of the second image 404 is $O_3$. From the time $T_0$ to the time $T_2$, the processor 16 decreases the opacity of the second image 404 and from the time $T_2$ to the time $T_4$, the processor 16 increases the opacity in the stepwise manner shown in the graph 800.

Graphs 700, 800 and 900 are just three exemplary embodiments of periodically repeating functions that may be used by the processor 16 to automatically vary the opacity of second image 404. The processor 16 may automatically cyclically adjust the opacity of the second image 404 according to other functions in other embodiments. The processor 16 may automatically cyclically vary the opacity of the second image 404 between a maximum value, such as the opacity $O_3$ and a minimum opacity, such as the opacity $O_1$ as shown in the FIGS. 7, 8 and 9. Additionally, according to other embodiments, the period of the cyclically varying function used to control the opacity of the second image 404 may be adjusted. The period of the cyclically varying function may be manually adjusted or the period may be automatically adjusted by the processor. For example, the period of the function may get longer over time, or the period of the function may get shorter over time. For example, when performing a registration between two or more images, it may be advantageous to have the period of the function change since the needs of the clinician may be different when making gross adjustments to the position of the second image 404 with respect to the first image 402 and when making fine adjustments to the position of the second image 404 with respect to the first image 402.

The graph 700, 800 and 900 all share a common period and have the same opacity values at the times demarcated on the x-axes of the graphs. However, the way that the processor 16 controls transitions between the times demarcated on the graphs is different in each of the embodiments shown.

FIG. 10 shows 4 exemplary screen shots that correspond to the times $T_0$, $T_1$, $T_2$, and $T_3$ shown in FIGS. 7, 8, and 9 according to an embodiment. It should be appreciated that the processor 16 may show intermediate images according to other embodiments. In other words, the processor 16 may show one or more images in between times $T_0$ and $T_1$. The processor 16 may show one or more images in between times $T_1$ and $T_2$. The processor 16 may show one or more images in between times $T_2$ and $T_3$. And the processor 16 may show one or more images in between times $T_3$ and $T_4$.

FIG. 10 includes an image 150 corresponding to the time $T_0$, an image 152 corresponding to the time $T_1$, an image 154 corresponding to the time $T_2$, and an image 156 corresponding to the time $T_3$. Each of the images 150, 152, 154, and 156 represents a composite image including the first image 402 and a second image 404. The second image 404 completely overlaps the first image 402 according to the embodiment shown in FIG. 10.

In the image 150, the second image 404 is displayed at the opacity $O_3$; in image 152, the second image 404 is displayed at the opacity $O_2$; in the image 154, the second image 404 is displayed at the opacity $O_1$; and in image 156, the second image 404 is displayed at the opacity $O_2$ again. As discussed above, the opacity of the second image 404 shown in FIG. 10 may be automatically varied by the processor 16 according to one of the functions graphically represented in FIG. 7, 8, or 9. FIG. 10 represents the change in opacity of the second image 404 over one complete period. It should be appreciated that the processor 16 may continue to automatically adjust the opacity of the second image as shown in FIG. 10 according to the same function for a period of time longer than one period.

According to many embodiment, the first image 402 and the second image 404 may represent image data acquired from different imaging modalities or they may represent image data acquired with different imaging modes using the same imaging modality. According to most embodiments, the first image 402 and the second image 404 contain different types of data. In order to help a clinician differentiate the first image 402 from the second image 404 in the composite image 406, the processor 16 may use a first colormap to display the first image data set as the first image and a second colormap, that is different from the first colormap, to display the second image data set as the second image.

The processor 16 may also control the opacity (and hence the transparency) of the second image 404 to allow the clinician to view both the first image 402 and the second image 404 in the region where the second image 404 overlaps the first image 402.

For example, image 150 shows the composite image at time T0 when the second image is at a maximum opacity level, represented by the opacity $O_3$. The maximum opacity level (i.e., minimum transparency level) makes the information in the second image 404 very easy for the clinician to discern at the cost of obscuring some of the information in the first image 402, which is the underlying image. The image 152 shows the second image 404 at opacity level $O_2$, which represents an opacity level in between the maximum opacity level $O_3$ and a minimum opacity level $O_1$. In the image 152, the intermediate opacity level $O_2$ allows the clinician to see some of the information in the first, underlying image 402 and some of the information in the second, overlying image 404. The image 154 shows the second image 404 at opacity level $O_1$, which represents the minimum opacity level (i.e., highest transparency level) according to an exemplary embodiment. The low opacity level allows the clinician to clearly see the structures and/or details represented in the first, underlying, image 402 in the area overlapped by the second image 404.

By automatically cyclically varying the opacity of the second image 404, this technique allows the clinician to alternate from clearly viewing all the details/structures in the second, overlying, image 404 and clearly viewing all the details/structures in the first, underlying, image 402. According to other embodiments, the processor 16 may control the display in a manner so that the colormap used for either the first image 402 or the second image 404 is cyclically varied at the same time the processor 16 cyclically varies the opacity of the second image 404.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method for visualizing overlapping images, the method comprising:
    accessing a first image data set and a second image data set, wherein the first image data set and the second image data set were acquired with one or more medical imaging systems;
    displaying a first image on a display device, wherein the first image comprises at least a portion of the first image data set and includes a structure;
    displaying a second image on the display device at the same time as the first image, wherein the second image comprises at least a portion of the second image data set and includes the structure, and wherein a portion of the second image overlaps the first image; and
    automatically cyclically varying an opacity of at least the portion of the second image that overlaps the first image, wherein automatically cyclically varying the opacity of at least the portion of the second image comprises automatically cyclically varying the opacity of the portion of the second image that overlaps the first image and not automatically cyclically varying the opacity of the portion of the second image that does not overlap the first image.

2. The method of claim 1, wherein the first image data set comprises first ultrasound image data acquired from a first ultrasound imaging mode, and the second image data set comprises second ultrasound image data acquired from a second ultrasound imaging mode, and wherein the second ultrasound imaging mode is different from the first ultrasound imaging mode.

3. The method of claim 2, wherein the first ultrasound imaging mode is a B-mode and the second ultrasound imaging mode is a color Doppler mode, and wherein first ultrasound image data and the second ultrasound image data are acquired in an interleaved manner.

4. The method of claim 1, wherein at least one of the first image data set and the second image data set is acquired in real-time.

5. The method of claim 1, wherein the portion of the second image that overlaps the first image has a nonuniform opacity.

6. The method of claim 1, wherein the portion of the second image that overlaps the first image has a uniform opacity.

7. The method of claim 1, wherein the opacity of at least the portion of the second image that overlaps the first image is automatically cyclically varied according to a periodically repeating function selected from the list consisting of: a sinusoidal function, a step function and a sawtooth function.

8. The method of claim 7, wherein the function has a period of between 1 second and 20 seconds.

9. The method of claim 8, wherein the period is user adjustable.

10. The method of claim 1, further comprising adjusting a position of the second image with respect to the first image while said automatically cyclically varying the opacity of at least the portion of the second image that overlaps the first image.

11. The method of claim 1, further comprising displaying the first image using a first colormap and displaying the second image using a second colormap that is different than the first colormap to help differentiate the first image from the second image.

12. The method of claim 1, wherein the first image data set is a first 3D data set and the second image data set is a second 3D data set, and wherein the first image is a first slice rendered from the first 3D data set and the second image is a second slice rendered from the second 3D data set.

13. A medical imaging workstation comprising:
a user input device;
a display device; and
a processor in electronic communication with both the user input and the display device, wherein the processor is configured to:
access a first image data set and a second image data set, where the first image data set and the second image data set were acquired with one or more medical imaging systems;
display a first image on the display device, wherein the first image comprises at least a portion of the first image data set and includes a structure;
display a second image on the display device at the same time as the first image, where the second image comprises at least a portion of the second image data set and includes the structure, and wherein a portion of the second image overlaps the first image; and
automatically cyclically vary an opacity of at least the portion of the second image that overlaps the first image, wherein the processor is configured to automatically cyclically vary the opacity of at least the portion of the second image by cyclically varying the opacity of the portion of the second image that overlaps the first image and not cyclically varying the opacity of the portion of the second image that does not overlap the first image.

14. The medical imaging workstation of claim 13, wherein the medical imaging workstation is a component of a medical imaging system.

15. The medical imaging workstation of claim 13, wherein the medical imaging workstation is a component of an ultrasound imaging system.

16. The medical imaging workstation of claim 13, wherein the processor is configured to cyclically vary the opacity of at least the portion of the second image that overlaps the first image according to a periodic function.

17. The medical imaging workstation of claim 13, wherein the processor is configured to display the first image using a first colormap and to display the second image using a second colormap, wherein the second colormap is different than the first colormap.

\* \* \* \* \*